US010712303B2

(12) United States Patent
Nackaerts

(10) Patent No.: US 10,712,303 B2
(45) Date of Patent: Jul. 14, 2020

(54) LIQUID EXPOSURE SENSING DEVICE AND CONTROLLER

(71) Applicant: NXP B.V., Eindhoven (NL)

(72) Inventor: Axel Nackaerts, Haasrode (BE)

(73) Assignee: NXP B.V., Eindhoven (NL)

( * ) Notice: Subject to any disclaimer, the term of this patent is extended or adjusted under 35 U.S.C. 154(b) by 162 days.

(21) Appl. No.: 16/057,227

(22) Filed: Aug. 7, 2018

(65) Prior Publication Data
US 2020/0049650 A1 Feb. 13, 2020

(51) Int. Cl.
*G01N 25/26* (2006.01)
*G01N 19/10* (2006.01)
*G01N 27/22* (2006.01)
*G01N 27/04* (2006.01)

(52) U.S. Cl.
CPC ......... *G01N 27/223* (2013.01); *G01N 27/048* (2013.01)

(58) Field of Classification Search
CPC .......... B81B 2201/0214; G01N 27/223; G01N 27/121; G01N 25/56
See application file for complete search history.

(56) References Cited

U.S. PATENT DOCUMENTS

| | | | |
|---|---|---|---|
| 4,352,059 A | 9/1982 | Suh et al. | |
| 6,346,888 B1 * | 2/2002 | Conrad | A01C 7/105 111/903 |
| 6,455,319 B1 * | 9/2002 | Lewis | G01N 27/126 422/68.1 |
| 7,688,215 B2 | 3/2010 | Vokey et al. | |
| 9,535,022 B1 * | 1/2017 | Meredith | G01N 22/00 |
| 10,390,672 B2 * | 8/2019 | Jung | A47L 11/4041 |
| 2002/0142477 A1 * | 10/2002 | Lewis | G01N 33/0031 436/151 |
| 2006/0034731 A1 * | 2/2006 | Lewis | G01N 27/121 422/88 |
| 2013/0151172 A1 | 6/2013 | Rao et al. | |
| 2013/0233073 A1 * | 9/2013 | Chen | G01N 27/223 73/335.02 |
| 2014/0218055 A1 | 8/2014 | Pion | |
| 2014/0298927 A1 * | 10/2014 | Allin | A61F 13/00051 73/865.8 |

(Continued)

OTHER PUBLICATIONS

Jain, Preeti; "Humidity Sensor"; retrieved from the Internet https://www.engineersgarage.com/articles/humidity-sensor; 12 pages (Aug. 6, 2018).

(Continued)

*Primary Examiner* — Alesa Allgood

(57) ABSTRACT

One example discloses a liquid exposure sensing device, including: a first sensor configured to be coupled to a reference material; wherein the first sensor configured to generate a first signal in response to either a liquid phase and/or vapor phase of a substance passing through the reference material; a second sensor configured to be coupled to an exposed material; wherein the second sensor configured to generate a second signal in response to the liquid phase and/or vapor phase of the substance passing through the exposed material; and a controller coupled to the first and second sensors and configured to generate a liquid detection signal in response to a time delay between the first signal and the second signal that exceeds a threshold time delay.

22 Claims, 8 Drawing Sheets

(56) References Cited

U.S. PATENT DOCUMENTS

2017/0086359 A1* 3/2017 Landphair ............... A01C 7/203
2018/0292340 A1* 10/2018 Koenig ................ G01N 27/124
2018/0321264 A1* 11/2018 Di Tullio .......... B01L 3/502715

OTHER PUBLICATIONS

Wikipedia; "Moisture Meter"; retrieved from the internet https://en.wikipedia.org/wiki/Moisture_meter; 3 pages (Aug. 6, 2018).

* cited by examiner

LIQUID EXPOSURE SENSING DEVICE AND CONTROLLER

The present specification relates to systems, methods, apparatuses, devices, articles of manufacture and instructions for detecting liquid exposure.

SUMMARY

According to an example embodiment, a liquid exposure sensing device, comprising: a first sensor configured to be coupled to a reference material; wherein the first sensor configured to generate a first signal in response to either a liquid phase and/or vapor phase of a substance passing through the reference material; a second sensor configured to be coupled to an exposed material; wherein the second sensor configured to generate a second signal in response to the liquid phase and/or vapor phase of the substance passing through the exposed material; and a controller coupled to the first and second sensors and configured to generate a liquid detection signal in response to a time delay between the first signal and the second signal that exceeds a threshold time delay.

In another example embodiment, the first and second sensors are impedance sensors and the first and second signals are impedance signals.

In another example embodiment, the first and second sensors are capacitive sensors and the first and second signals are capacitive signals.

In another example embodiment, amplitudes of the capacitive signals increase in response to an increase in the vapor phase of the substance.

In another example embodiment, the first and second sensors are conductive sensors and the first and second signals are conductive signals.

In another example embodiment, amplitudes of the conductive signals increase in response to an increase in the liquid phase of the substance.

In another example embodiment, the first sensor is configured to be in galvanic contact with the reference material, and the second sensor is configured to be in galvanic contact with the exposed material.

In another example embodiment, the exposed material and the reference material are a same type of material.

In another example embodiment, the exposed material and the reference material are different types of materials.

In another example embodiment, the exposed material and the reference material have a same thickness of material.

In another example embodiment, the exposed material and the reference material have different thicknesses of materials.

In another example embodiment, the exposed material is configured to be in direct contact with the liquid phase of the substance before the reference material is in direct contact with the liquid phase of the substance.

In another example embodiment, the first and second sensors are configured to measure both capacitance and conductance; and the controller is configured to generate the liquid detection signal in response to the first signal and the second signal exceeding a threshold capacitance time delay and a third signal and a fourth signal from the first and second sensors exceeding a threshold conductance time delay.

In another example embodiment, the controller is configured to generate a liquid condensation signal in response to either the first or second signals exceeding an amplitude threshold signal level.

In another example embodiment, the controller includes a memory element that records when and/or whether the liquid phase and/or vapor phase of the substance passed through the exposed material and/or the reference material during one or more legs of a physical transport journey.

In another example embodiment, further comprising a coating separating the first sensor and the reference material from an ambient environment; wherein the coating is permeable to the vapor phase, but not to the liquid phase.

In another example embodiment, both the first and second sensors are responsive to the vapor phase of the substance.

In another example embodiment, either the exposed material and/or the reference material is at least one of: paper, cardboard, cloth, mesh, or fiber.

In another example embodiment, further comprising a package having a cavity; wherein the exposed material lines an inside surface of the cavity; and wherein the reference material is outside of the cavity.

In another example embodiment, further comprising a package having a cavity; wherein the exposed material lines an outside surface of the cavity; and wherein the reference material is inside of the cavity.

In another example embodiment, further comprising a substrate; wherein the first sensor is on one side of the substrate and the second sensor is on an opposite side of the substrate.

According to an example embodiment, a liquid exposure controller circuit, comprising: a controller circuit configured to be coupled to first and second sensors; wherein the first sensor is configured to be coupled to a reference material, and to generate a first signal in response to either a liquid phase and/or vapor phase of a substance passing through the reference material; wherein the second sensor is configured to be coupled to an exposed material, and to generate a second signal in response to the liquid phase and/or vapor phase of the substance passing through the exposed material; and wherein the controller circuit is configured to generate a liquid detection signal in response to a received time delay between the first signal and the second signal that exceeds a threshold time delay.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

Figure 1:
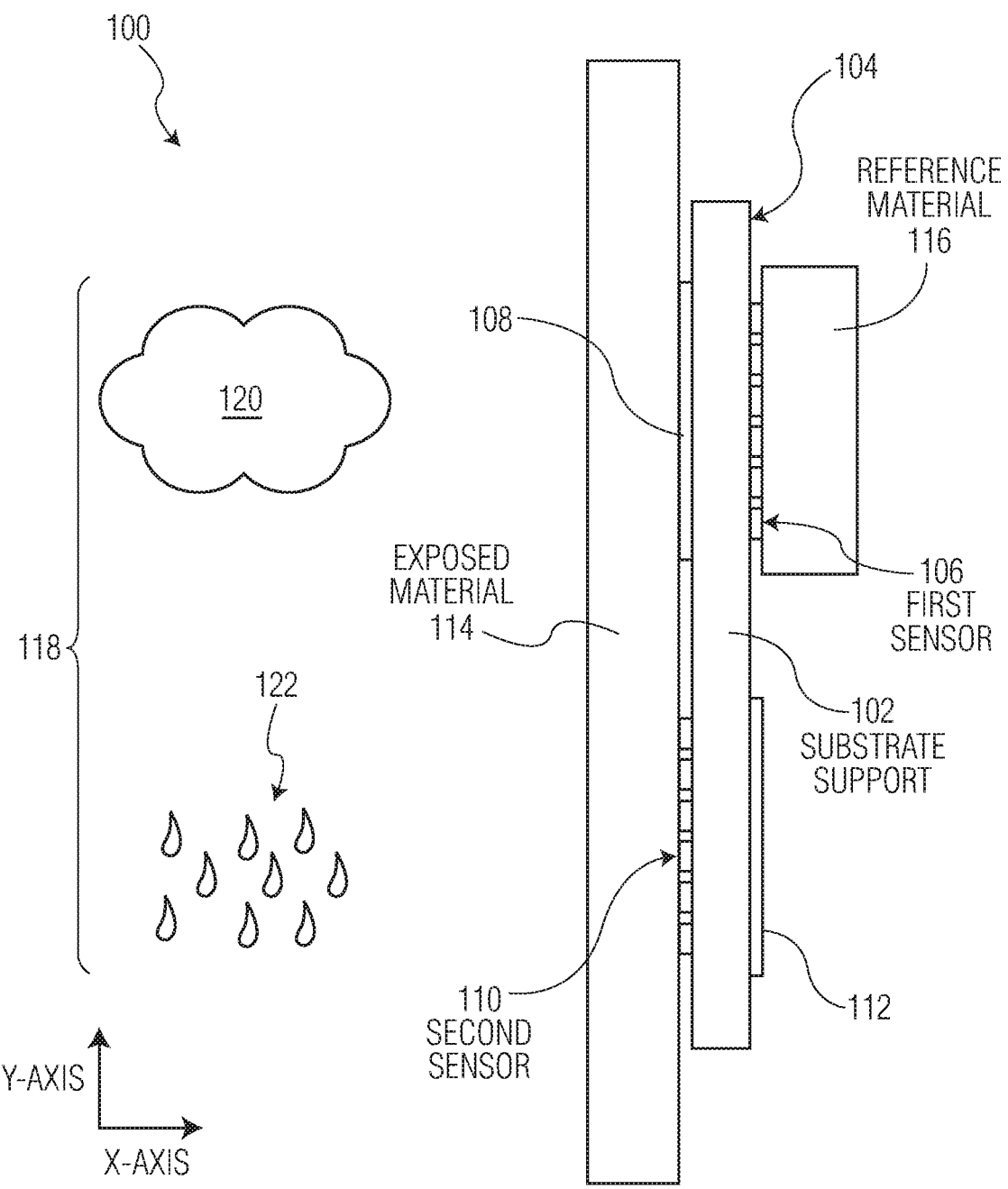
FIG. 1 is an example of a liquid exposure sensing device.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Moisture detection in cardboard packaging materials, and detection of wetting by liquid water; and the ability to detect high humidity conditions, are important parameters (next to temperature) for the monitoring of logistics operations; however, current moisture meters, and relative humidity measurement systems are concerned with the measurement of moisture, and not in finding the cause of the change in moisture.

In many logistical, warehousing, and delivery applications, package moisture changes due to relative humidity are allowed, but changes due to wetting are not. Note that direct contact with water, for example, is not the same as 100% humidity and condensation which can occur without direct wetting. For example, moving a package from cold storage to a hot, high humidity environment will result in condensation but not direct wetting as defined here. However, splashing liquid, rain, spillage, etc. are forms of direct wetting.

Whether a package has experienced high humidity or wetting can be very important in the shipment and storage of various pharmaceuticals, parcel post items, and other important packages. Customers often pay extra money to verify their package did not get wet during transit, or to identify if it did. Such information can have an effect on package integrity, quality control, and for insurance claims.

Now discussed are example embodiments of a liquid exposure sensing device that if applied to a package, a medical device, or other object to be monitored, differentiates between whether they were exposed to and/or dropped in water or another liquid, or whether the package only experienced a high humidity ambient environment resulting in perhaps condensation during one or more legs of its transport journey.

The liquid exposure sensing device includes, in some example embodiments, two materials (i.e. an exposed material, a material under test, etc. and a reference material) where either they are isolated as such that any wetting is not experiences by both materials at the same time, and/or the moisture content of both is allowed to change due to changes in relative humidity, but not due to wetting (e.g. the "reference material is protected from getting wet). Such protection from being wetted is different from normal encapsulation that not only prevents wetting of a reference material, but also prevents exposure to relative humidity.

FIG. 1 is an example of a liquid exposure sensing device 100. The liquid exposure sensing device 100 includes a substrate support 102, a sensor substrate 104, a first sensor 106 coupled to a reference material 116, a second sensor 110 coupled to an exposed material 114, a first ground plate 108 for shielding the first sensor 106 from the exposed material 114, and a second ground plate 112 for shielding the second sensor 110 from the reference material 116.

The exposed material 114 (e.g. material under test) is exposed to an ambient environment to be monitored. In such ambient environment can be either a vapor phase 120 or a liquid phase 122 of a substance 118. In one example embodiment, the exposed material 114 is an outward surface of a package.

Note that the vapor phase 120 of the substance 118 is in some examples dominated by porosity forces in the materials 114, 116, and the liquid phase 122 of the substance 118 is dominated by capillary forces in the materials 114, 116.

The reference material 116 is semi-protected from the ambient environment to be monitored (e.g. can be exposed to the vapor phase 120 but not the liquid phase 122 of the substance 118). In one example embodiment, the reference material 116 is somewhere inside the package. For example, if the package has a cavity, the exposed material 114 can line an outside surface of the cavity and the reference material 116 is inside of the cavity. Alternatively, the exposed material 114 can line an inside surface of the cavity and the reference material 116 is outside of the cavity.

In various embodiments, the package and either of the materials 114, 116 can be made of paper, cardboard, cloth, mesh, and/or fiber.

In some example embodiments, the substrate 104 is a flexible material (e.g. 50 um thin PET foil) and also hosts other circuit components (e.g. a battery, controller, integrated circuit, etc.). The support 102 over which the substrate 104 is folded can be a 1 mm thick foam spacer. In an alternate example embodiment the support 102 and substrate 104 can be a printed circuit board.

In some example embodiments, either or both the support 102 and substrate 104 repel particular substances 118 (e.g. water) depending upon which substances 118 the liquid exposure sensing device 100 is designed to monitor for. The first sensor 106 in some examples is on one side of the substrate 104 and the second sensor 110 is on an opposite side of the substrate 104.

In some example embodiments, the liquid exposure sensing device 100 is permanently attached to a packaging (e.g. via glue or adhesive) and disposable.

In the liquid exposure sensing device 100 the first sensor 106 is configured to generate a first signal in response to either a liquid phase and/or vapor phase of a substance passing through (i.e. liquid and/or gas diffusion) the reference material 116. The second sensor 110 is configured to generate a second signal in response to the liquid phase and/or vapor phase of the substance passing through the exposed material 114.

A controller (see FIG. 2) is coupled to the first and second sensors 106, 110 and is configured to generate a liquid detection signal in response to a time delay between the first signal and the second signal that exceeds a threshold time delay (see FIGS. 4-8 for examples). With the two sensors 106, 110, liquid exposure can be detected using either just the two capacitance measurements, just the two conductance measurements, or both sets of capacitance and conductance measurements.

The first and second sensors 106, 110 can be impedance sensors, capacitive sensors and/or conductive sensors.

Note in some example embodiments, capacitance measurement increases are correlated with increasing vapor concentration level (e.g. humidity if the substance is water) since a dielectric strength of the vapor phase 120 of a substance 118 varies with the vapor concentration level. Similarly conductance measurement increases are correlated with increasing liquid phase 122 condensation, since condensation acts as a short circuit and shortens the path length between electrodes, thus increasing conductance.

Thus if the first and second sensors 106, 110 are capacitive sensors and the first and second signals are capacitive signals, then amplitudes of the capacitive signals increase in response to an increase in the vapor phase of the substance. In some example embodiments, the sensors 106, 110 are configured to measure capacitance at 1 MHz.

Also if the first and second sensors 106, 110 are conductive sensors and the first and second signals are conductive signals, then amplitudes of the conductive signals increase in response to an increase in the liquid phase of the substance. In some example embodiments, the sensors 106, 110 are configured to measure conductance at D.C.

In some example embodiments, the first sensor 106 is configured to be in galvanic contact with the reference material 116, and the second sensor 110 is configured to be in galvanic contact with the exposed material 114.

In some example embodiments, the first and second sensors 106, 110 are configured to measure both capacitance and conductance; and, the controller 206 is configured to generate the liquid detection signal in response to the first signal and the second signal exceeding a threshold capacitance time delay and a third signal and a fourth signal from the first and second sensors 106, 110 exceeding a threshold conductance time delay.

The controller 206 includes a memory element that records when and/or whether the liquid phase and/or vapor phase of the substance passed through the exposed material 114 and/or the reference material 116 during one or more legs of a physical transport journey.

In some example embodiments, the exposed and reference materials 114, 116 have a same thickness. In other examples, the materials 114, 116 have different thicknesses. Also, in some example embodiments, the exposed and reference materials 114, 116 are of a same type of material. In other examples, the materials 114, 116 are different. In still other example embodiments, the liquid exposure sensing device 100 uses matched exposed and reference materials 114, 116 having both a same thickness and made of a same type of material.

When different types and/or thicknesses of materials 114, 116 are used, adjustments in the controller's 206 circuitry, logic, instructions, etc. may need to be made in response to a temperature behavior of the materials 114, 116. For example dielectric constants may change with temperature, as may absorption/desorbtion characteristics. These properties of the materials 114, 116 can be stored in the memory element as well.

Figure 2:
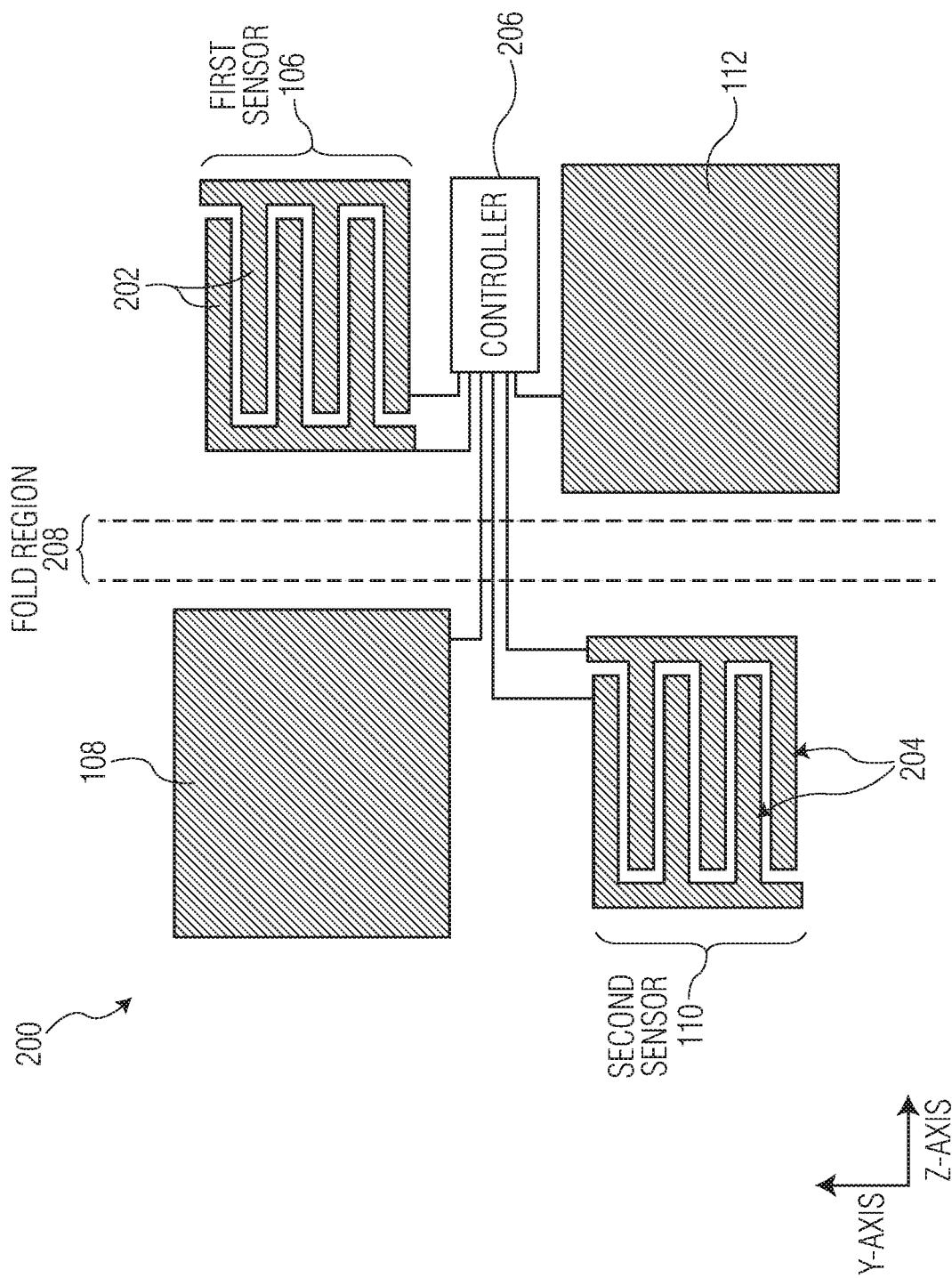
FIG. 2 is an example of a portion of the liquid exposure sensing device before folding.

FIG. 2 is an example of a portion 200 of the liquid exposure sensing device 100 before folding. The portion 200 of liquid exposure sensing device 100 includes the first sensor 106 having a first electrode pair 202, the second sensor 110 having a second electrode pair 204, a controller 206 perhaps having a memory element (not shown), and a fold region 208.

The electrode pairs 202, 204 (e.g. "finger capacitors") can be printed or etched interdigitated electrode pairs of equal size, made of conductive material, each about 1 cm², with spacing between the fingers similar to the thickness of materials 114, 116 (e.g. etched aluminum, 6 fingers are 0.5 mm wide and have 1 mm spacing, 3 fingers connected to each side).

The electrodes 202, 204 are in various example embodiments not be covered by insulating material, so at to permit galvanic contact between electrodes 202, 204 and packaging material. If either of the electrode pairs 202, 204 are covered with an insulating material, primarily a capacitance measurement is possible from that electrode pair.

The ground plates 108, 112 can also be printed or etched ground planes of equal size. The ground plates 108, 112 are in some examples larger than the interdigitated electrodes by at least the thickness of the support 102, and extend equally on each side (e.g. 12 mm by 12 mm). The first ground plate 204 shields exposed material 110 from first electrode pair 202, and the second ground plate 208 shields reference material 116 from second electrode pair 206.

The controller 206 measures the signals from the two sensors 106, 110 at predefined time intervals to capture any changes in capacitance and/or conductance. In some example embodiments, the controller 206 operates the first and second sensors 106, 110 at a frequency best able to permit detection of wetting by one or more liquids to be monitored. For example a frequency less than 100 kHz could be used to detect liquid water and humidity. The controller 206 can be configured to measure an ambient temperature, and a simple or a complex impedance (i.e. capacitance (μF) and/or conductance (mho)).

A power source (not shown) (e.g. a printed battery) may also be included on the substrate 104.

The electrode pairs 202, 204 and ground plates 108, 112 are in some example embodiments printed on a flexible substrate 104 which is then folded about the support 102 along fold lines in the fold region 208 and held in place with an adhesive or glue. Then the reference material 116 is attached to the first sensor 106 and the second (e.g. exposed material) sensor 110 and the first ground plate 108 are attached to the exposed material 114 (e.g. inside or outside of a package).

Figure 3:
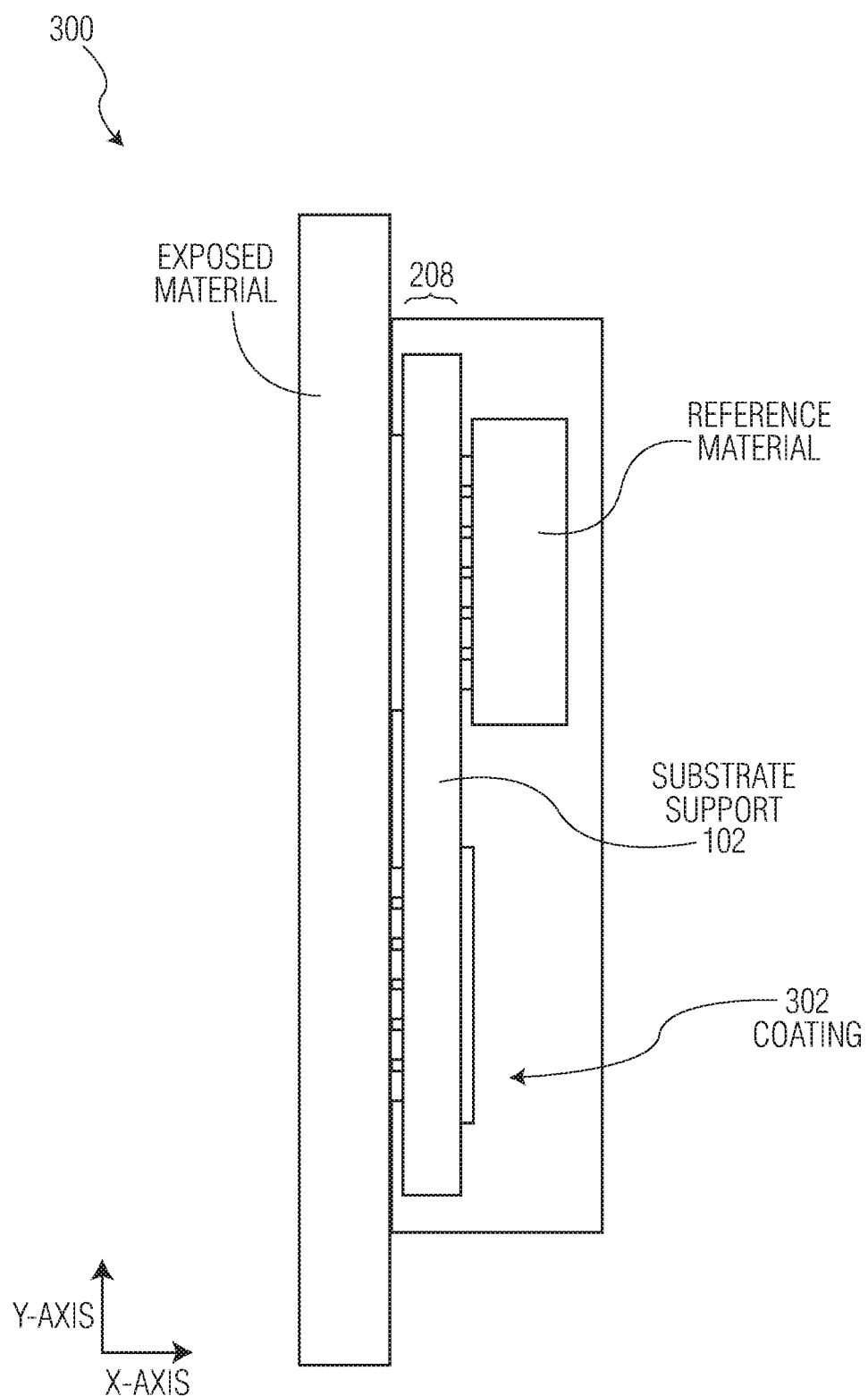
FIG. 3 is an example of the liquid exposure sensing device after coating.

FIG. 3 is an example 300 of the liquid exposure sensing device 100 after coating. A coating 302 separating the first sensor 106 and the reference material 116 from an ambient environment is applied in some examples. The coating is permeable to the vapor phase 120 of the substance 118, but not to the liquid phase 122. Thus the coating 302 is vapor-permeable, but watertight (e.g. like a breathable membrane/fabric).

Figure 4A:
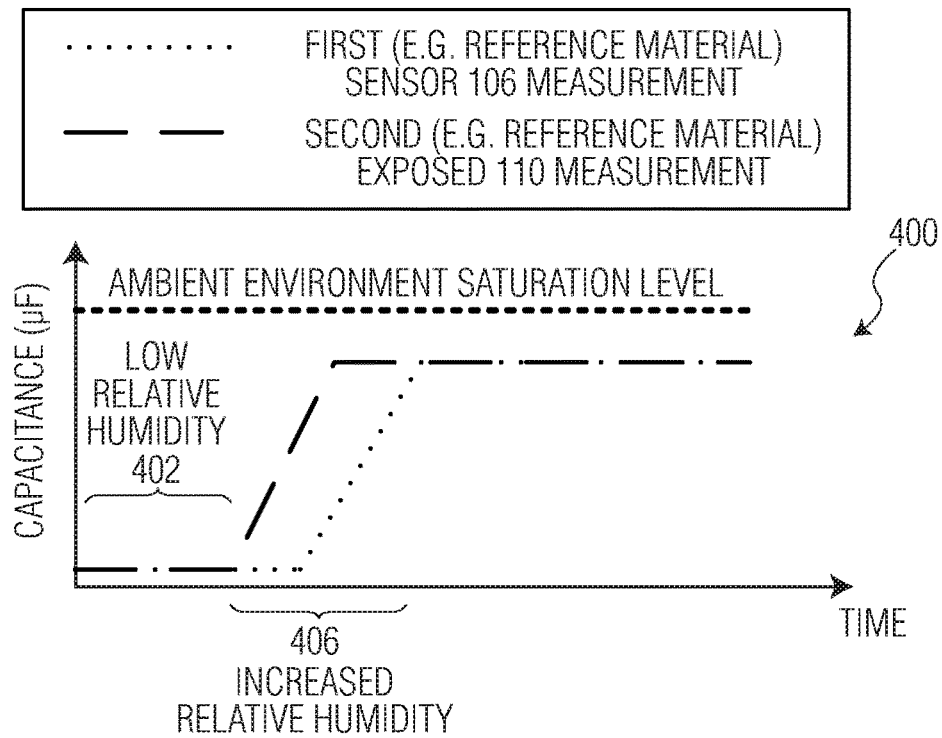
FIGS. 4A and 4B are an example first set of first and second signals from first and second sensors.
Figure 4B:
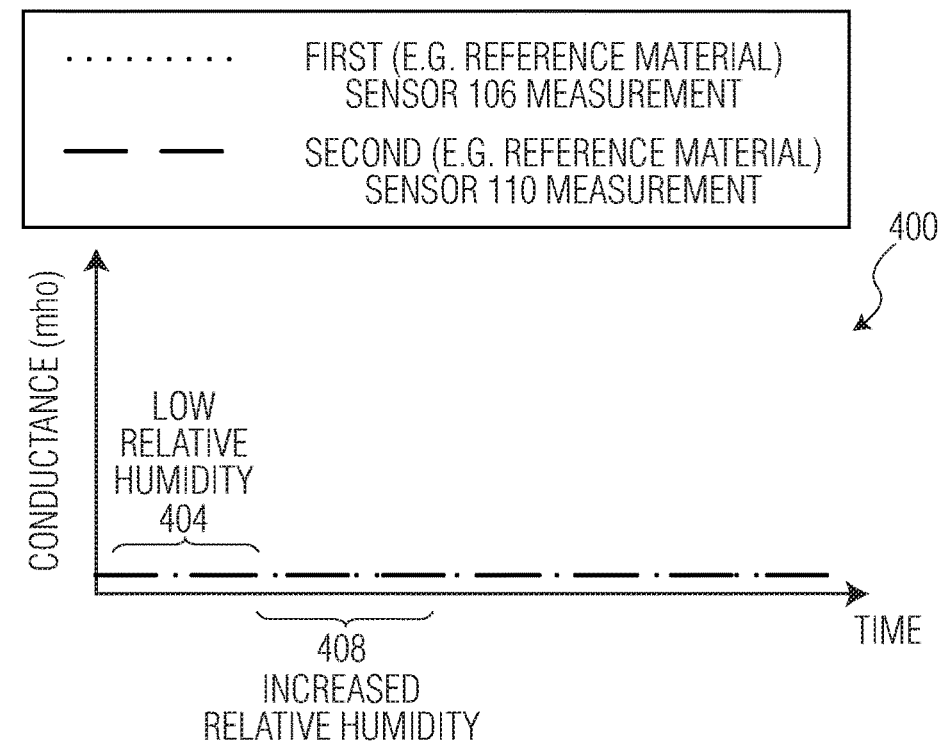

FIGS. 4A and 4B are an example first set of first and second signals 400 from first and second sensors 106, 110. The first set of sensor signals 400 show regions 402 and 404 of low relative humidity, and regions 406 and 408 of increasing relative humidity.

In some example embodiments like shown in FIG. 4A, the first (e.g. reference material) sensor's 106 capacitance changes lag behind the second (e.g. exposed material) sensor's 110 capacitance changes, having a time constant based on (e.g. limited by) water vapor diffusion through the exterior packaging material.

If both inside and outside capacitance and conductance measurements are low (i.e. regions 402 and 404 in FIGS. 4A and 4B), then low moisture level due to low relative humidity. However, if both inside and outside capacitance increased compared to previous measurement period, but conductance remains low (i.e. regions 406 and 408 in FIGS. 4A and 4B), then increased moisture level is due to an increased relative humidity.

Figure 5A:
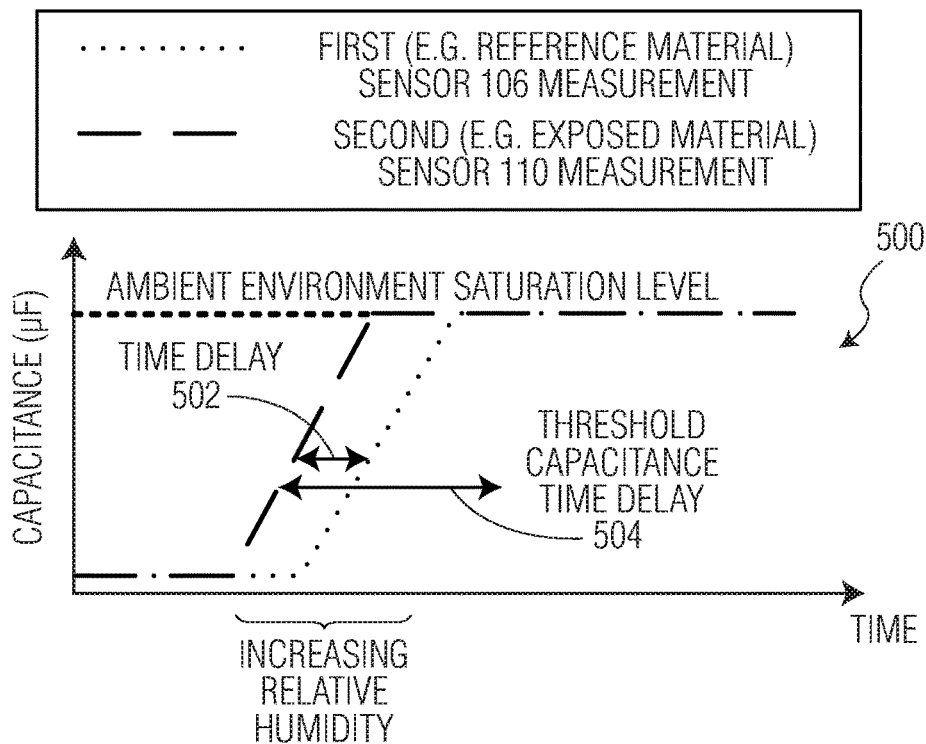
FIGS. 5A and 5B are an example second set of first and second signals from first and second sensors.
Figure 5B:
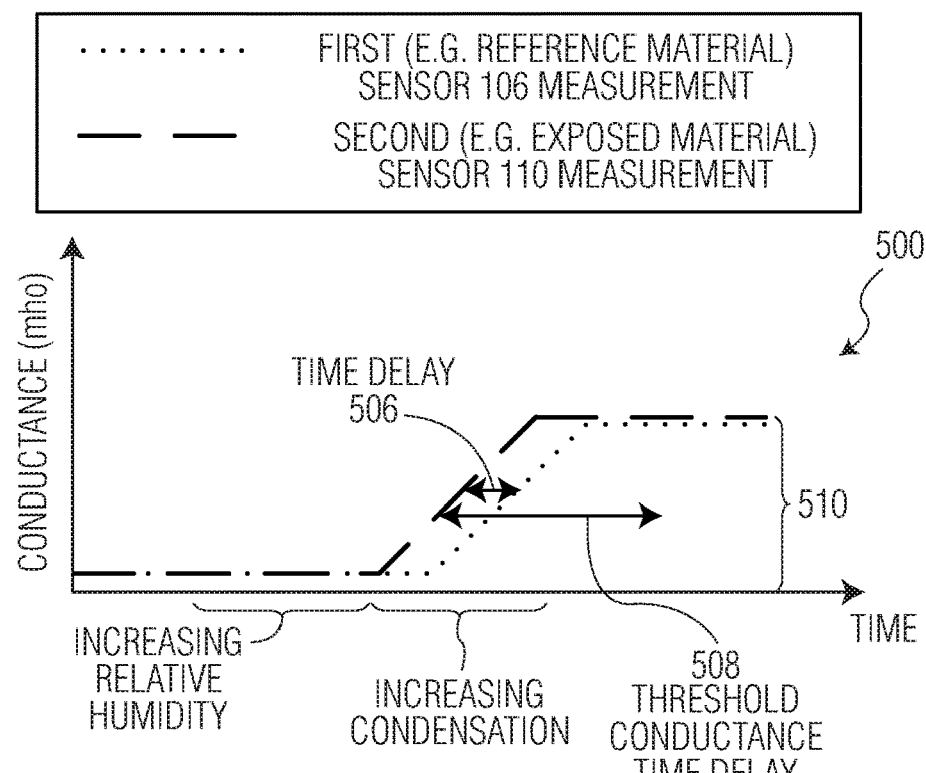

FIGS. 5A and 5B are an example second set of first and second signals 500 from first and second sensors 106, 110. The second set of sensor signals 500 show a time delay 502, a threshold capacitance time delay 504, a time delay 506, a threshold capacitance time delay 508, and a condensation level 510.

Capacitance changes of both sensors 106, 110 having a time delay 502 less than the threshold capacitance time delay 504 and/or conductance changes of both sensors 106, 110 having a time delay 506 less than the threshold conductance time delay 508 are correlated with changes in relative humidity of the exposed material 114.

For example, liquid water vapor can permeates through the exposed material 114 relatively quickly and thus changes the signals from both sensors relatively quickly as well.

If excessive humidity results in condensation, the conductance measurements will also have a time delay 506 less than the threshold conductance time delay 508 (i.e. both sensors will register a large increase in conductance of the materials relatively quickly).

If both inside and outside capacitance high and conductivity increased (see FIGS. 5A and 5B), then an increase in relative humidity has resulted in increasing condensation and the capacitance values correspond to an ambient environment saturation level.

Figure 6A:
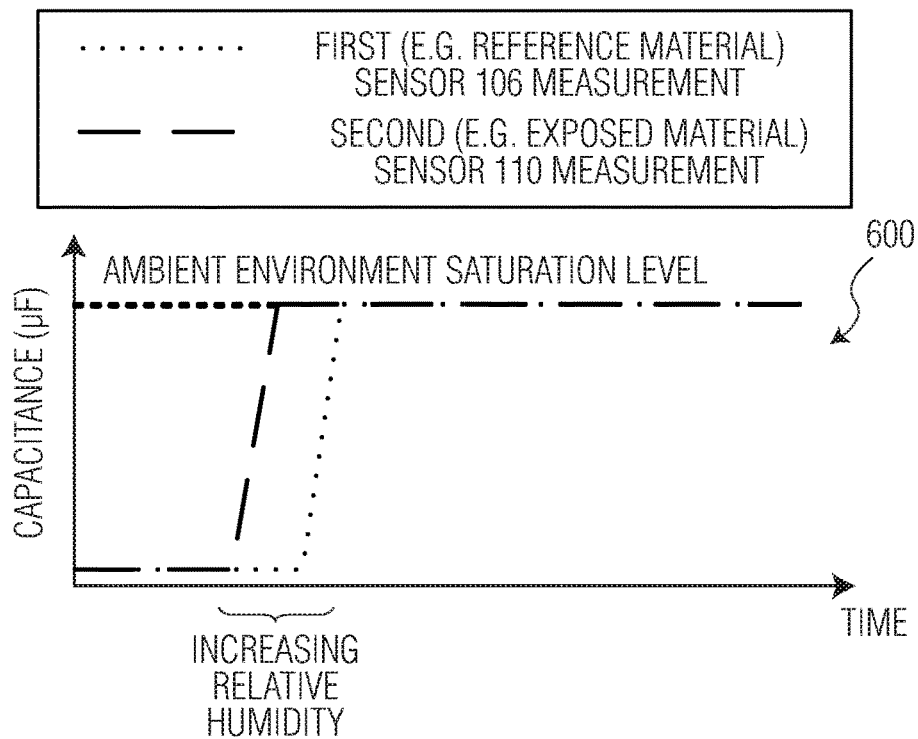
FIGS. 6A and 6B are an example third set of first and second signals from first and second sensors.
Figure 6B:
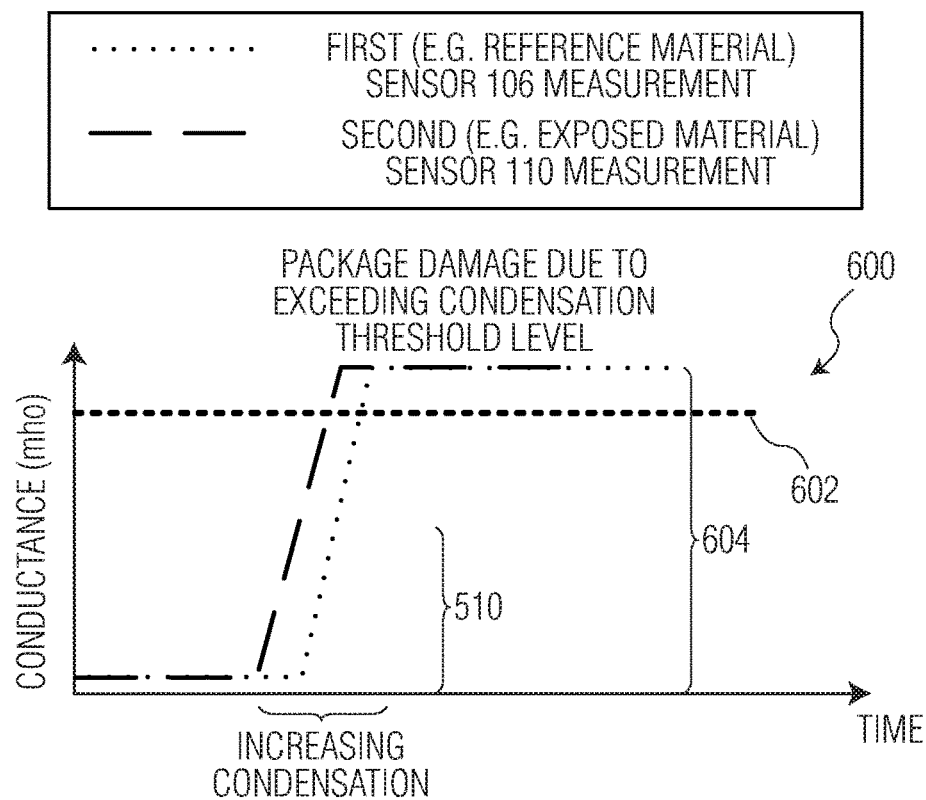

FIGS. 6A and 6B are an example third set of first and second signals 600 from first and second sensors 106, 110. The third set of sensor signals 600 shows a condensation threshold level 602 and a conductance 604. These Figures present a special case of FIGS. 5A and 5B, where there is a great deal of condensation.

If both inside and outside conductance 604 exceeds the condensation threshold level 602, then the condensation caused by very high humidity will likely cause structural damage to the packaging material. The actual damage threshold 602 depends upon the packaging material used (e.g. paper packaging could have a lower threshold than a cloth packaging).

In some example embodiments, this scenario correlates with slowly increasing temperature (i.e. package was cold and comes in contact with humid air, and slowly heats up.).

Figure 7A:
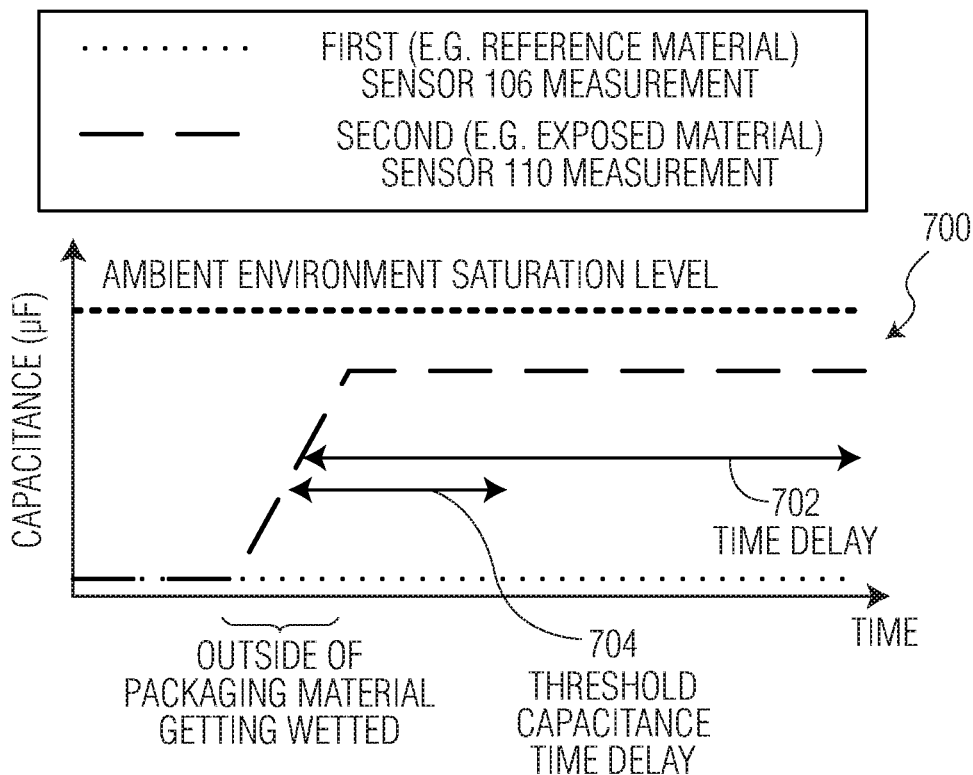
FIGS. 7A and 7B are an example fourth set of first and second signals from first and second sensors.
Figure 7B:
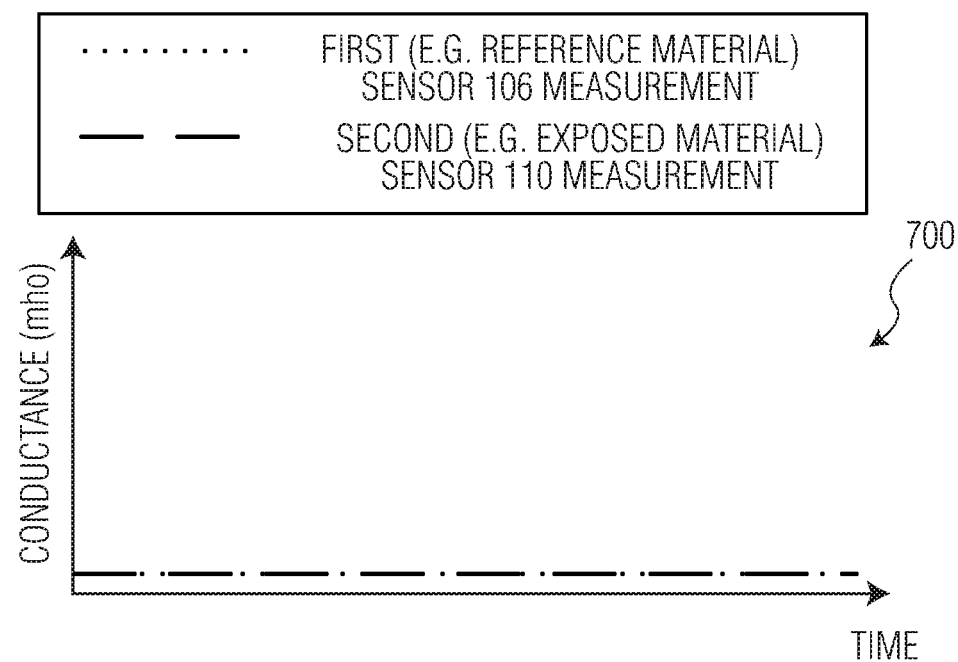

FIGS. 7A and 7B are an example fourth set of first and second signals 700 from first and second sensors 106, 110. The fourth set of sensor signals 700 include a time delay 702 and a threshold capacitance time delay 704.

Capacitance changes of the first (i.e. reference material) sensor 106 having a time delay 702 greater than the threshold capacitance time delay 704 as compared to capacitance changes of the second (e.g. exposed material) sensor 110 (see FIG. 7A) are correlated with the liquid phase 122 of the substance 118 contacting the exposed material 114.

In this example, the exposed material 114 has been directly in contact with the liquid substance and is becoming wetted as the liquid diffused through the exposed material 114 (e.g. perhaps due to e.g. external rain, internal contents spillage, etc.).

Since there is no substantial physical contact between the exposed material 114 and the reference material 116, the reference material 116 will not substantially be in contact with the liquid substance, and thus there will be a large time delay 702 between the capacitive (see FIG. 7A) responses of the first and second sensors 106, 110.

By comparing the time delay 702 to the threshold capacitance time delay 704, the controller 206 can discriminate between condensation wetting due to only high humidity, and direct liquid wetting that could negatively affect the quality of the device or substance being carried by and/or surrounded by the exposed material 114 (e.g. package).

In another example embodiment, if the first sensor's 106 capacitance is low, the first sensor's 106 conductance is low, the second sensor's 110 capacitance is high, and the second sensor's 110 conductance is low (see FIGS. 7A and 7B), then the exposed material 114 has been contact with the liquid phase 122 of the substance 118. Here either there is a low amount of liquid, or this is an early stage of further wetting to come. The timescale is dominated by the diffusion of water through the packaging material.

Thus, by comparing the time delay 702 to the threshold capacitance time delay 704 of the first and second signals, the controller 206 can discern between rapid wetting of the exposed material 114 (e.g. via liquid immersion, rain, spillage, etc.) from the exposed material 114 only being in a humid environment.

In some example embodiments wetting causes only the second (e.g. on the exposed material) sensor 110 to get wet while the first (e.g. reference material) sensor 106 stays dry or is at least delayed in getting wet.

Figure 8A:
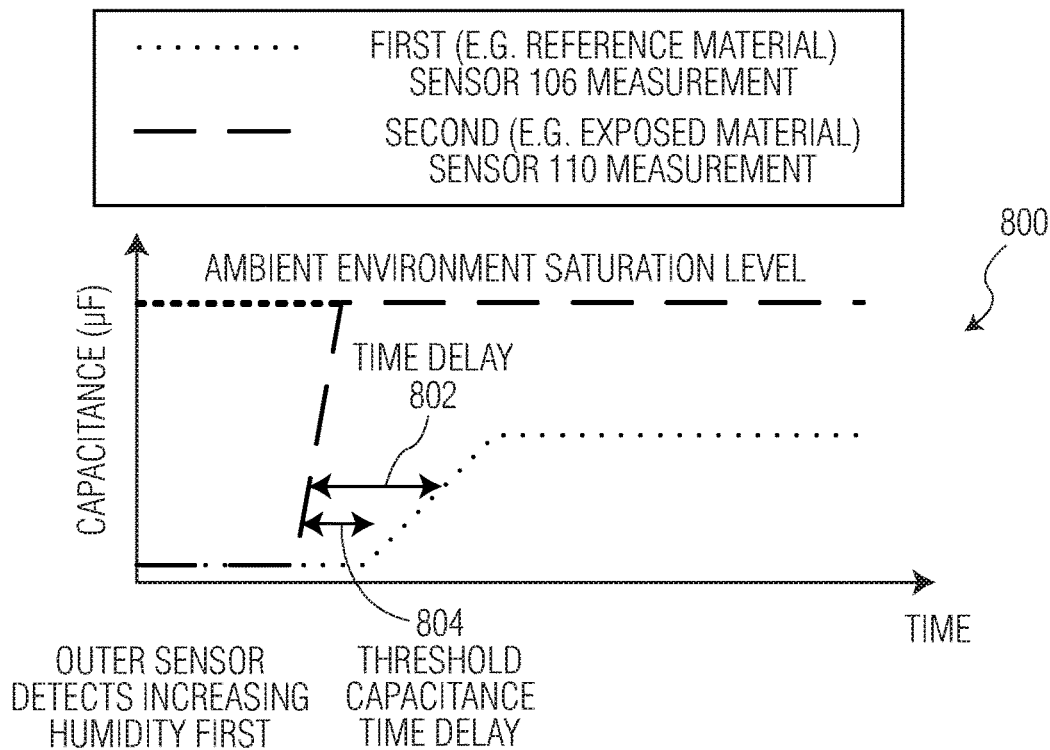
FIGS. 8A and 8B are an example fifth set of first and second signals from first and second sensors.
Figure 8B:
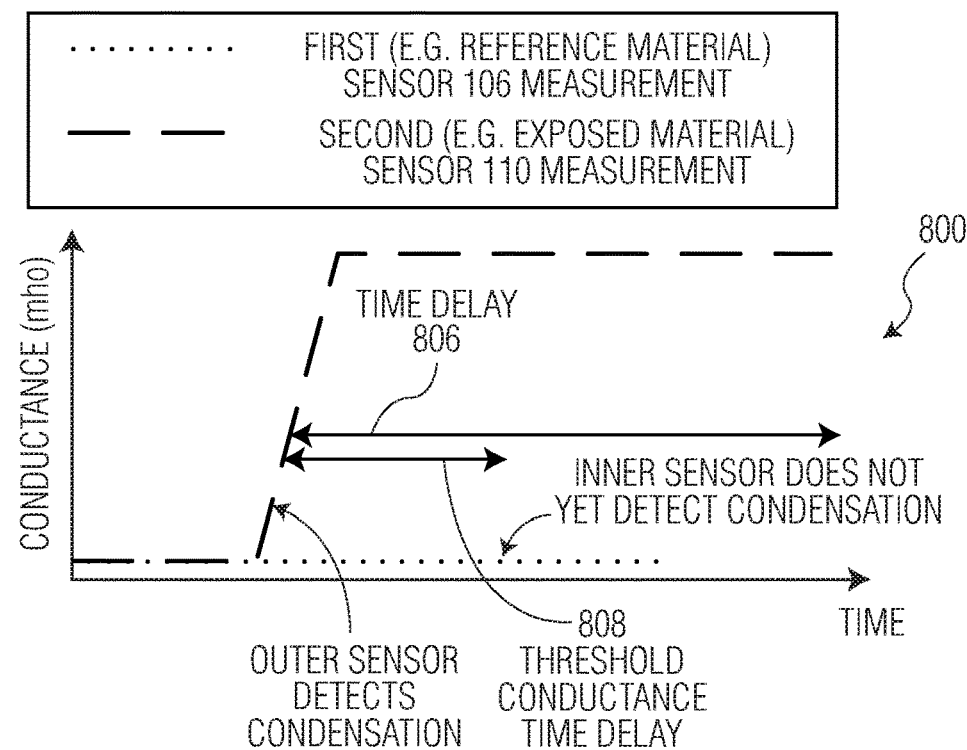

FIGS. 8A and 8B are an example fifth set of first and second signals 800 from first and second sensors 106, 110. The fifth set of sensor signals 800 includes a time delay 802, a threshold capacitance time delay 804, a time delay 806, and a threshold conductance time delay 808.

Either capacitance and/or conductance changes of either the first or second sensors 106, 110 having time delays 802, 606 greater than the threshold capacitance or conductance time delays 804, 808 are correlated with the liquid phase 122 of the substance 118 contacting the exposed material 114.

This example can be understood as extending the fourth set of sensor signals 700 (see FIGS. 7A and 7B) in time thereby yielding the fifth set of sensor signals 800. Here the capacitance signals have reached an ambient environment saturation level (e.g. 100% humidity) (see FIG. 8A) and now the condensation signals are also beginning to increase (see FIG. 8B).

Is this example 800, the exposed material 114 has been in direct contact with the liquid substance for a longer time than shown before in FIGS. 7A and 7B and is becoming even further wetted as the liquid continues to diffuse through the exposed material 114.

These disparate measurements between the first and second sensors 106, 110 are correlated with a wetted exterior packaging material and not due to an increase in ambient environment humidity.

In some example embodiments, the controller 206 makes this determination if the first sensor's 106 capacitance is low, the first sensor's 106 conductance is low, the second sensor's 110 capacitance is high, and the second sensor's 110 conductance is high (see FIGS. 8A and 8B), then the exposed material 114 is experiencing both humidity saturation and condensation; while the reference material 116 is only beginning to experience an increase in humidity due to an increase in local (e.g. inside package) relative humidity caused by an evaporation of the liquid phase 122 of the substance 118 from the inside surface of the exposed material 114. FIG. 8B shows that there is not yet any condensation measured by the first sensor 106 since the first sensor 106 is not yet wetted.

Note that in some example embodiments, both condensation and exterior wetting exposures will lead to small but permanent changes in the exposed material's 114 characteristics (e.g. $value_{new} < > value_{old}$). Thus after a condensation event, both inside and outside materials 114, 116 may return to different but still equal measurement values (e.g. inside=outside); however in case of wetting the inside and outside materials 114, 116 may not equally return to their prior measurement values (e.g. inside< >outside). Thus in such embodiments even if no controller 206 measurement was made during a wetting event, the wetting event can still be detected afterwards.

The above example embodiments can be applied to Smart Sensors. Packaging (e.g. Food, Parcel, Medical, etc.) manufacturers may also be interested in these example embodiments for measuring various types of moisture. The above example embodiments not only report moisture levels and temperature, but also distinguish between the causes of such moisture (e.g. direct wetting vs. ambient humidity).

While the discussion above gave examples for a single liquid sensing device applied to a package, other applications are possible. For example: multiple liquid sensing devices could be applied to various locations on a package. Also, additional and/or redundant liquid exposure sensing devices 100 could be added.

While "outside wet" but "inside dry" embodiments have been often discussed above, the liquid exposure sensing device 100 can also be applied to "inside wet" but "outside dry" packages that monitor for internal food or medical spillage.

The liquid exposure sensing device 100 can also be applied to monitor an object, food or device as it proceeds through various manufacturing steps to ensure quality control.

The liquid exposure sensing device 100 can also be a part of an RFID/NFC tag. An additional antenna is then needed for communication. It would be similar to temperature logging NFC tags as we have developed over the last few years, but also monitor moisture. I do not consider that a fundamental part of the invention.

Various instructions and/or operational steps discussed in the above Figures can be executed in any order, unless a specific order is explicitly stated. Also, those skilled in the art will recognize that while some example sets of instructions/steps have been discussed, the material in this specification can be combined in a variety of ways to yield other examples as well, and are to be understood within a context provided by this detailed description.

In some example embodiments these instructions/steps are implemented as functional and software instructions. In other embodiments, the instructions can be implemented either using logic gates, application specific chips, firmware, as well as other hardware forms.

When the instructions are embodied as a set of executable instructions in a non-transient computer-readable or computer-usable media which are effected on a computer or machine programmed with and controlled by said executable instructions. Said instructions are loaded for execution on a processor (such as one or more CPUs). Said processor includes microprocessors, microcontrollers, processor modules or subsystems (including one or more microprocessors or microcontrollers), or other control or computing devices. A processor can refer to a single component or to plural components. Said computer-readable or computer-usable storage medium or media is (are) considered to be part of an article (or article of manufacture). An article or article of manufacture can refer to any manufactured single component or multiple components. The non-transient machine or computer-usable media or mediums as defined herein excludes signals, but such media or mediums may be capable of receiving and processing information from signals and/or other transient mediums.

It will be readily understood that the components of the embodiments as generally described herein and illustrated in the appended figures could be arranged and designed in a wide variety of different configurations. Thus, the detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

What is claimed is:

1. A liquid exposure sensing device, comprising:
a first sensor configured to be coupled to a reference material;
wherein the first sensor configured to generate a first signal in response to either a liquid phase and/or vapor phase of a substance passing through the reference material;
a second sensor configured to be coupled to an exposed material;
wherein the second sensor configured to generate a second signal in response to the liquid phase and/or vapor phase of the substance passing through the exposed material; and
a controller coupled to the first and second sensors and configured to generate a liquid detection signal in response to a time delay between the first signal and the second signal that exceeds a threshold time delay.

2. The sensor of claim 1:
wherein the first and second sensors are impedance sensors and the first and second signals are impedance signals.

3. The sensor of claim 1:
wherein the first sensor is configured to be in galvanic contact with the reference material, and the second sensor is configured to be in galvanic contact with the exposed material.

4. The sensor of claim 1:
wherein the exposed material and the reference material are a same type of material.

5. The sensor of claim 1:
wherein the exposed material and the reference material are different types of materials.

6. The sensor of claim 1:
wherein the exposed material and the reference material have a same thickness of material.

7. The sensor of claim 1:
wherein the exposed material and the reference material have different thicknesses of materials.

8. The sensor of claim 1:
wherein the exposed material is configured to be in direct contact with the liquid phase of the substance before the reference material is in direct contact with the liquid phase of the sub stance.

9. The sensor of claim 1:
wherein the first and second sensors are configured to measure both capacitance and conductance; and
wherein the controller is configured to generate the liquid detection signal in response to the first signal and the second signal exceeding a threshold capacitance time delay and a third signal and a fourth signal from the first and second sensors exceeding a threshold conductance time delay.

10. The sensor of claim 1:
wherein the controller is configured to generate a liquid condensation signal in response to either the first or second signals exceeding an amplitude threshold signal level.

11. The sensor of claim 1:
wherein the controller includes a memory element that records when and/or whether the liquid phase and/or vapor phase of the substance passed through the exposed material and/or the reference material during one or more legs of a physical transport journey.

12. The sensor of claim 1:
further comprising a coating separating the first sensor and the reference material from an ambient environment;
wherein the coating is permeable to the vapor phase, but not to the liquid phase.

13. The sensor of claim 1:
wherein both the first and second sensors are responsive to the vapor phase of the substance.

14. The sensor of claim 1:
wherein either the exposed material and/or the reference material is at least one of: paper, cardboard, cloth, mesh, or fiber.

15. The sensor of claim 1:
further comprising a package having a cavity;
wherein the exposed material lines an inside surface of the cavity; and
wherein the reference material is outside of the cavity.

16. The sensor of claim 1:
further comprising a package having a cavity;
wherein the exposed material lines an outside surface of the cavity; and
wherein the reference material is inside of the cavity.

17. The sensor of claim 1:
further comprising a substrate;
wherein the first sensor is on one side of the substrate and the second sensor is on an opposite side of the substrate.

18. The sensor of claim 1:
wherein the first and second sensors are capacitive sensors and the first and second signals are capacitive signals.

19. The sensor of claim 18:
wherein amplitudes of the capacitive signals increase in response to an increase in the vapor phase of the substance.

20. The sensor of claim 1:
wherein the first and second sensors are conductive sensors and the first and second signals are conductive signals.

21. The sensor of claim 20:
wherein amplitudes of the conductive signals increase in response to an increase in the liquid phase of the substance.

22. A liquid exposure controller circuit, comprising:
a controller circuit configured to be coupled to first and second sensors;
wherein the first sensor is configured to be coupled to a reference material, and to generate a first signal in response to either a liquid phase and/or vapor phase of a substance passing through the reference material;
wherein the second sensor is configured to be coupled to an exposed material, and to generate a second signal in response to the liquid phase and/or vapor phase of the substance passing through the exposed material; and
wherein the controller circuit is configured to generate a liquid detection signal in response to a received time delay between the first signal and the second signal that exceeds a threshold time delay.

* * * * *